(12) United States Patent
Schneider

(10) Patent No.: US 6,995,091 B2
(45) Date of Patent: Feb. 7, 2006

(54) PROCESS FOR CHEMICALLY MECHANICALLY POLISHING WAFERS

(75) Inventor: Germar Schneider, Dresden (DE)

(73) Assignee: Infineon Technologies AG, Munich (DE)

( * ) Notice: Subject to any disclaimer, the term of this patent is extended or adjusted under 35 U.S.C. 154(b) by 269 days.

(21) Appl. No.: 10/304,131

(22) Filed: Nov. 25, 2002

(65) Prior Publication Data

US 2003/0100144 A1 May 29, 2003

(30) Foreign Application Priority Data

Nov. 23, 2001 (DE) .............................. 101 57 452

(51) Int. Cl.
*H01L 21/302* (2006.01)

(52) U.S. Cl. .......................... 438/693; 438/14; 216/84; 216/86; 216/89; 356/945

(58) Field of Classification Search ................ 438/8, 438/14, 690, 691, 692, 693, 747, 753; 216/84, 216/86, 88, 89, 90, 91
See application file for complete search history.

(56) References Cited

U.S. PATENT DOCUMENTS

| 6,121,147 A | 9/2000 | Daniel et al. | |
|---|---|---|---|
| 6,246,474 B1 * | 6/2001 | Cerni et al. | .................. 356/335 |
| 6,762,832 B2 * | 7/2004 | Fisher et al. | ................. 356/300 |

OTHER PUBLICATIONS

Schneider et al., Spectrochimica Acta B Part B (1995), 1557-71.*
Wilson et al., Handbook of Multilevel Metallization for Integrated Circuits, 1993, Noyes Publications, pp. 429-430.*
Susanne Hauptkorn et al.: "Determination of Silicon in Titanium Dioxide and Zirconium Dioxide by Electrothermal Atomic Absorption Spectrometry Using the Slurry Sampling Technique", *Journal of Analytical Atomic Spectrometry*, Mar. 1993, vol. 9, pp. 463-468.
Germar Schneider et al.: "Slurry and liquid sampling using electrothermal atomic absorption spectrometry for the analysis of zirconium dioxide based materials", *Spectrochimica Acta* Part B vol. 50, 1995, pp. 1557-1571.

* cited by examiner

*Primary Examiner*—Nadine G. Norton
*Assistant Examiner*—Eric B. Chen
(74) *Attorney, Agent, or Firm*—Laurence A. Greenberg; Werner H. Stemer; Ralph E. Locher

(57) ABSTRACT

The invention relates to a process for chemically mechanically polishing and grinding wafers. The CMP slurry that is used for grinding is analyzed using slurry atomic absorption spectroscopy. This allows rapid and sensitive analysis of the slurry constituents, in particular of interfering ions. The process can be automated and makes it possible to process wafers with a constant quality. Furthermore, rapid fault analysis or optimization of the process parameters used during the grinding is possible.

11 Claims, 1 Drawing Sheet

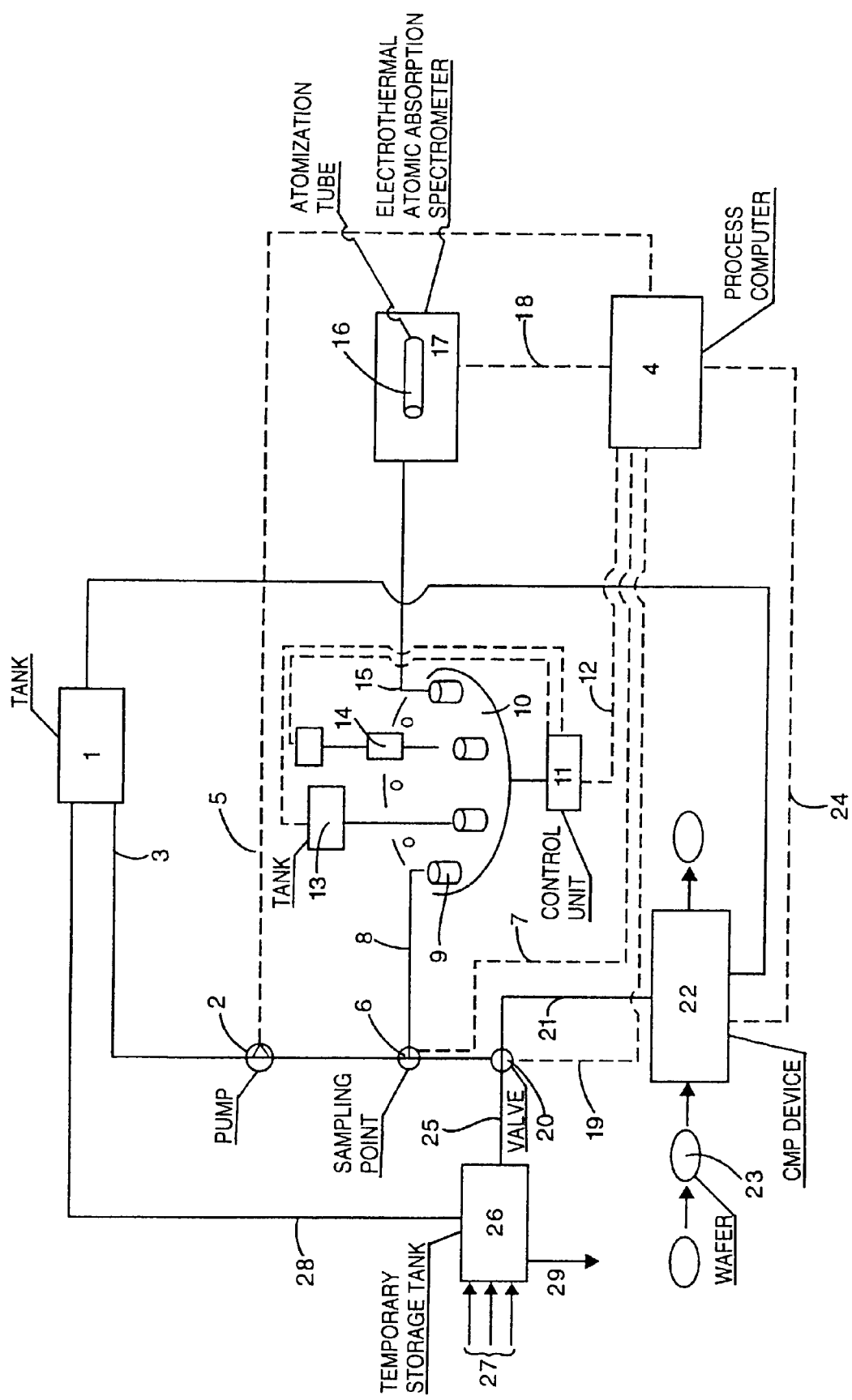

PROCESS FOR CHEMICALLY MECHANICALLY POLISHING WAFERS

BACKGROUND OF THE INVENTION

Field of the Invention

The invention relates to a process for chemically mechanically polishing wafers.

The production of microchips is based on what are known as wafers, which consist of ultra pure silicon, gallium arsenide, silicon carbide or related materials. Electronic components are integrated in these disk-like wafers in a layer formed by processes such as exposure, etching, deposition, implantation and sputtering. By way of example, first of all a photosensitive resist layer is applied to the wafer, and this resist is then exposed in sections using short-wave light. Developing using a developer medium allows the resist layer to be removed in the exposed regions and the substrate to be uncovered. Then, a suitable etching medium, such as fluorine plasma, can be used to etch a trench, for example, into the uncovered regions of the wafer. The trench can then be filled with a dielectric and a counterelectrode in order to fabricate a storage capacitor. Then, by way of example, a transistor can be built up by depositing further layers and is used to control the charge state of the storage capacitor. In this way, layered electronic components are built up, in which process currently feature sizes of less than 0.2 $\mu$m are achieved. Very short-wave radiation is used to image such small structures on the photoresist. Therefore, only a very low depth of focus is available for the exposure. To avoid faults or blurring during the exposure, the wafer surface undergoes chemical mechanical polishing after certain process steps in order to provide a surface that is as planar as possible. The photoresist can then be applied over the entire surface of the wafer in a constant layer thickness. The chemical mechanical polishing (CMP) is carried out in substantially automated fashion in CMP devices. A CMP installation of this type includes a polishing surface, a supporting surface for a wafer and a feed for a polishing abrasive, which is also known as the CMP slurry. The surface of the wafer can be removed in amounts ranging from nanometers to micrometers by using the CMP slurry. The surface is removed both mechanically and by a chemical action. The CMP slurry is a suspension of a water-insoluble powder comprising particles with a size in the $\mu$m range that consist of a hard material, for example, silicon dioxide, silicon nitride, silicon carbide or metal oxides, such as calcium oxide, and which has been formed into a slurry in an aqueous or ammonia-containing solution. In addition the CMP slurry may also contain further components, for example, fluoride ions. During the polishing, the composition of the CMP slurry changes, since the surface of the wafer is mechanically abraded and chemical reactions take place between the components of the CMP slurry and the components of the wafer that are present at the surface of the wafer. Furthermore, the solid constituents that are present in the slurry contain impurities that are leached out during the polishing operation. Therefore, over the course of time, interfering ions that may affect the grinding action accumulate in the CMP slurry. To achieve a uniform quality and yield of the microchips, currently certain parameters of the CMP slurry, such as for example, the size and size distribution of the particles present in the CMP slurry, are tested before the slurry is released for chemical mechanical polishing. The CMP slurry is then used for a defined use period. This use period is determined empirically, i.e. is based on experience. By analyzing the particle size and size distribution of the particles of the powder used for polishing and by standardizing the use period, it is possible to achieve a substantially constant quality and yield of microchips. Nevertheless, fluctuations that cannot be satisfactorily explained do occur in the quality of the microchips produced. This causes problems because microchips take a very long time to produce, and under certain circumstances, a fault analysis may only be possible at a very much later time, for example, after the conductive connections required for a test have been produced in suitable further process steps. Therefore, an increase in productivity would be possible if defects could be detected and eliminated at an early stage. By way of example, in addition to physical analysis, an analysis of the chemical composition of the CMP slurry would also be conceivable with a view to achieving improved process control. The operations which occur during chemical polishing are very complicated chemical and physical events which can currently only be partially explained. To make it possible to understand the deviations that occur in chemical mechanical polishing and to be able to draw conclusions from them as to the production conditions and possible fault sources, the grinding and polishing operation must, if possible, be observed continuously. However, a chemical analysis in particular of the interfering ions, in particular the interfering elements that are critical for the semiconductor products, such as Al, Ca, Cr, Cu, Fe, K, Mg, Na, Ni, Zn, as well as other ions in the slurry matrix, is very difficult. In addition to the high solids content, the constant presence of one or more elements present as the main constituent of the CMF slurry also causes problems. In principle, chemical analysis methods available include atomic absorption spectroscopy (AAS), mass spectrometry (MS, ICP-MS) and atomic emission spectrometry (OES). However, these analysis processes require decomposition of the solid constituents of the sample taken from the CMP slurry, which is time-consuming and leads to an increase in the fault tolerance. Particularly on account of the time that elapses between sampling and the availability of the analysis result, online control of the grinding process with regard to the composition of the CMP slurry is not possible. Especially with MS and OES, furthermore, the high matrix content leads to problems and therefore has an adverse effect on the detection limits.

SUMMARY OF THE INVENTION

It is accordingly an object of the invention to provide a process for chemically mechanically polishing wafers, which overcomes the above-mentioned disadvantages of the prior art methods of this general type.

In particular, it is an object of the invention to provide a process for chemically mechanically polishing wafers that enables a more uniform quality of the processed wafers to be obtained.

With the foregoing and other objects in view there is provided, in accordance with the invention, a process for chemically mechanically polishing wafers. The process includes steps of: providing a CMP slurry having a solvent and at least one component; defining a range of values for a level of the component in the CMP slurry; taking a slurry sample from the CMP slurry; with an electrothermal absorption spectrometer, performing electrothermal slurry atomic absorption spectrometry to obtain a determined level of the component in the slurry sample; comparing the determined level of the component with the range of values for the level of the component; if the determined level of the component is within the range of values for the level of the component, feeding the CMP slurry to a CMP device and polishing a wafer using the CMP slurry in the CMP device; and if the determined level of the component is outside the range of values for the level of the component, triggering a signal.

In accordance with an added feature of the invention, the process includes homogenizing the slurry sample using ultrasound before carrying out the step of performing the electrothermal slurry atomic absorption spectrometry to obtain the determined level of the component in the slurry sample.

In accordance with an additional feature of the invention, the step of homogenizing the slurry sample is performed at a frequency of between 40 and 50 kHz, at a power of 2 to 10 watts, and for a period of 10 to 60 seconds.

In accordance with another feature of the invention, the component is provided as an interfering ion; and the step of defining the range of values is performed such that the range of values is less than 10 ppm.

In accordance with a further feature of the invention, the step of defining the range of values is performed such that the range of values is less than 100 ppb.

In accordance with a further added feature of the invention, the step of defining the range of values is performed such that the range of values is less than 1 ppb.

In accordance with another added feature of the invention, the the interfering ion is provided as an ion of at least one element selected from a group consisting of Al, Ca, Cr, Cu, Fe, K, Mg, Na, Ni, and Zn.

In accordance with yet an added feature of the invention, an automatic sampler is used to feed the slurry sample to the electrothermal absorption spectrometer.

In accordance with yet an additional feature of the invention after triggering the signal, the CMP slurry is fed to a temporary storage device.

In accordance with yet another feature of the invention, the process includes: defining a maximum deviation for the component; for the CMP slurry that has been fed to the temporary storage device, determining a difference between the determined level and the range of values for the level; if the difference is less than the maximum deviation, topping off or topping up the component until the level of the component lies within the range of values; and if the difference is greater than the maximum deviation, discarding the CMP slurry.

In accordance with yet a further feature of the invention, the process includes carrying out the step of performing the electrothermal slurry atomic absorption spectrometry on line so that the CMP slurry can be fed to the CMP device.

In accordance with a concomitant feature of the invention a process computer is used to control the steps of: performing the electrothermal slurry atomic absorption spectrometry to obtain the determined level of the component in the slurry sample; and feeding of the CMP slurry to the CMP device.

The object is achieved by a process for the chemical mechanical polishing of wafers, in which: a CMP slurry having a solvent and at least one component is provided; ranges of values for the level of the at least one component of the CMP slurry are defined; a slurry sample is taken from the CMP slurry; and the level of the at least one component in the CMP slurry is determined in the slurry sample by using electrothermal slurry atomic absorption spectrometry. The determined level of the at least one component is compared with the range of values defined for the level of that at least one component, and (a) if the determined level of the at least one component lies within the range of values defined for the level of the at least one component, the CMP slurry is fed to a CMP device and a wafer is polished using the CMP slurry in the CMP device; or (b) if the determined level of the at least one component is outside the range of values defined for the level of the at least one component, a signal is triggered.

The essential feature of the grinding process is considered to lie in the quality control of the CMP slurry used by analysis using electrothermal slurry atomic absorption spectrometry (slurry ETAAS). This analysis technique does not require decomposition of the CMP slurry. Rather, the CMP slurry can be fed directly to an electrothermal atomic absorption spectrometer for analysis, i.e. without the solid constituents having to be separated off. Therefore, an analysis result is available within a short time and can be used to influence the further grinding operation.

Electrothermal slurry atomic absorption spectrometry is currently used primarily for research applications relating mainly to the development of methods. There have not previously been any applications of these methods in industrial fields, in particular, for process control.

For example, S. Hauptkorn, G. Schneider and V. Krivan, J. Anal At. Spectrom., 1993, 9, 563–468 describe a process for detecting silicon in titanium dioxide and zirconium oxide by electrothermal slurry atomic absorption spectroscopy (ETAAS). This analysis process gives detection limits for silicon of 7 $\mu$g/g in titanium dioxide and of 2 $\mu$g/g in zirconium dioxide. To attenuate matrix interference effects, calcium nitrate is added to the samples as an accompanying substance. The use of $^{47}$Ca and $^{97}$Zr as radiotracers made it possible to analyze the characteristics of zirconium and calcium in a graphite tube during the ashing, atomization and cleaning processes.

Furthermore, G. Schneider and V. Krivan, Spectrochim. Acta Part B, 1995, 40, 1557–1571 describe a process for the electrothermal atomic absorption spectroscopy of Al, Ca, Cd, Co, Cr, Cu, Fe, K, Li, Mg, Mn, Na, Si and Zn in pulverulent zirconium dioxide and yttria-stabilized zirconium dioxide in slurry samples. The detection limits of electrothermal slurry atomic absorption spectrometry are in the range from 1–20 ng/g for the elements Ca, Cd, K, Mg, Na and Zn and in the range from 20–200 ng/g for Al, Co, Cr, Cu, Fe, Li, Mn and Ni. The detection limit for Si is 2 $\mu$g/g.

Atomic absorption spectrometers which are customary per se can be used for electrothermal slurry atomic absorption spectrometry. It is possible to use both graphite tube spectrometers and spectrometers with an atomization tube made from other materials, such as tungsten or tungsten carbide. The CMP slurry sample is injected and the analysis is then carried out using a standard temperature program. For this purpose, it is appropriate for sample quantities of 2 to 100 $\mu$l to be added to the atomization tube. The solvent is evaporated at the start of the analysis cycle. For this purpose, the sample is heated at a temperature in the range from 50 to 200° C. for from 30 seconds to 5 minutes. If the CMP slurry includes low-volatility organic constituents, an ashing step can be carried out, for which purpose the sample is heated at from 300 to 2300° C. for from 30 second to 5 minutes. In general, CMP slurries substantially contain inorganic salts and ceramic abrasives, and consequently there is generally no need for an ashing step. This is followed by atomization of the sample, for which purpose the sample is heated to from 1500 to 2600° C. for from 3 to 10 seconds. Finally, to complete the heating, the atomization tube is heated at from 2400 to 2700° C. for between 2 to 10 seconds, before being cooled back to room temperature over approximately 1 to 5 minutes. The ranges given for the quantity of sample, the temperature and the duration of the individual steps are only intended to represent guidelines and may also be modified as a function of the AAS appliance used and the CMP slurry which is to be analyzed.

Standard processes are used for background correction. To compensate for interference during the atomization, by way of example it is possible to use a deuterium or Zeeman background correction. The calibration of the measurement may be carried out externally against a calibration curve put together using standard solutions or preferably by using a standard addition method. In the latter calibration method, the standards are each added to the sample, so that it is also possible to take account of influences from matrix interference in the measurement result.

To control the chemical mechanical grinding, first of all ranges within which the relevant component may be present in the CMP slurry are defined. These ranges of values can be determined, for example, from measurement curves which have likewise been compiled by using slurry ETAAS and can be compiled from measured values determined at set intervals over the course of a grinding operation. If the inventive process is used directly for monitoring the grinding process, the ranges of values can also be optimized during production. For this purpose, by way of example, initially an arbitrary range of values can be selected, and this range is then optimized by observing the measured parameters and by correlating them with changes in the quality of the processed wafers.

Slurry ETAAS can in particular also be used to detect interfering ions, such as Al, Ca, Cr, Cu, Fe, K, Mg, Na, Ni and Zn, but also other ions down to ppm or even ppb quantities, as well as the solid constituents of the CMP slurry. This allows very accurate control of the grinding process. Rapid fault analysis and further optimization of the grinding process are made possible even while production is ongoing.

After the level of at least one specific component, for example, one of the interfering ions mentioned above, in the CMP slurry has been determined using slurry ETAAS, this value is compared with the range of values which has previously been defined for this component. This may be carried out manually by operating staff or preferably using a process computer. Then, the further processing of the CMP slurry is controlled on the basis of this comparison. If the value determined for the component lies within the previously defined range of values, the CMP slurry is fed to a CMP device, and a wafer that is in position in the device is polished using the CMP slurry. If the measured value of the component is outside the previously defined range of values, a signal is triggered. This signal can be used to control the further production process. By way of example, the production or polishing operation can be stopped, or the signal can also be regarded as an indication that the CMP slurry is becoming exhausted, so that it can be replaced with fresh CMP slurry.

A range of less than 10 ppm, preferably less than 1 ppm, particularly preferably less than 100 ppb, especially preferably less than 10 ppb and most preferably less than 1 ppb, is defined as a range of values for the level of interfering ions in the CMP slurry. If the level of interfering ions in the CMP slurry exceeds this upper limit of the range of values, according to the invention, a signal in triggered. Therefore, the range of values can apply to the sum of all the interfering ions and also to specific individual interfering ions. For example, it is also possible to define different ranges of values for different interfering ions.

The interfering ion whose level in the CMP slurry is observed in order to monitor the polishing process is preferably an ion of at least one element which is selected from the group consisting of Al, Ca, Cr, Cu, Fe, K, Mg, Ma, Ni, Zn. These ions have a particularly strong effect on the chemical and physical characteristics of the CMP slurry. In principle, however, it is also possible to observe other ions. The term interfering ions is used to refer to the ions that are not present as main constituents of the CMP slurry, i.e. which are not planned to be used in the production of the CMP slurry. Therefore, which ions are considered to be interfering ions is dependent on the composition of the CMP slurry. For example, aluminum ions may act as interfering ions in a CMP slurry that contains particles Of $SiO_2$, while they will be regarded as a main constituent in a CMP slurry which contains particles of $Al_2O_3$.

Despite their small dimensions, the solid constituents of the CMP slurry tend to settle over the course of time. To obtain reproducible measured values, the slurry sample is preferably homogenized by ultrasound before the level of the component in the CMP slurry is determined. The homogenization is carried out, for example, in such a manner that first of all the slurry sample is added to a sampling vessel, and then an ultrasound probe is introduced into the sample for homogenization purposes immediately before the sample is taken. However, other methods of ultrasonic homogenization are also possible. For example, the sampling vessel may also be placed into an ultrasound bath in order for the sample to be homogenized.

The ultrasound treatment for homogenization of the sample is preferably carried out at a frequency of between 40 and 50 kHz and a power of 2 to 10 watts for a period of 10 to 60 seconds.

According to a particularly preferred embodiment, the slurry sample is fed to the atomic absorption spectrometer using an automatic sampler. Using an automatic sampler on the one hand allows the determination of values to be substantially automated and on the other hand increases the accuracy when the sample is taken.

If the value determined for the component of interest does not lie within the range of values that has previously been defined for the component, a signal is triggered, as has already been explained above. This signal can be used to control the further process sequence. According to a preferred embodiment, after the signal has been triggered, the CMP slurry is fed to a temporary storage device. The CMP slurry that has been temporarily stored can then be neutralized and concentrated so that it can then be disposed of.

According to a particular embodiment, the CMP slurry can also be worked up in such a manner that it can be returned to the grinding process. For this purpose, first of all a maximum deviation is defined for the at least one component. Then, the difference between the determined level and the defined range of values is determined for the CMP slurry that has been fed to the temporary storage device. If the difference is less than the maximum deviation, the component is topped up until its level is once again within the range of values defined for this component. This is particularly suitable for those components in the CMP slurry that are consumed during the grinding operation. However, if the difference is greater than the maximum deviation, the CMP slurry is discarded. This applies, for example, to interfering ions that are introduced into the CMP slurry during the grinding. In this way, the consumption of slurry can be reduced further while maintaining the same quality of the wafers produced, with the result that costs can be reduced and the process can also be made more environmentally friendly, on account of the lower level of chemical pollution.

Accurate control of the grinding and polishing operation can be achieved if the level of the at least one component is determined online for feeding the CMP slurry to the CMP device. The advantage of the slurry ETAAS used in the inventive polishing process is the rapid availability of the measured values. This allows rapid reaction to deviations in the composition of the CMP slurry. Therefore, the online measurement allows the polishing process to be influenced directly.

The inventive process is eminently suitable for automation. For this purpose, the determination of the level of the at least one component of the CMP slurry and the feeding of the CMP slurry to the CMP device is controlled using a process computer. The process computer may also control further process steps involved in the production of the wafer, and in this case too feedback or fault analysis from subsequent process steps that follow the grinding and polishing of the wafer is possible.

The slurry atomic absorption spectrometry is also eminently suitable for quality control during the production of CMP slurries. In this way it is possible to check quickly and without major outlay whether, for example, interfering ions have already been introduced into the CMP slurry via raw materials. Therefore, as well as testing the size and size distribution of the particles present in the CMP slurry, slurry ETAAS can also be suitably used to test its chemical composition in order for the CMP slurry to be released.

Other features which are considered as characteristic for the invention are set forth in the appended claims.

Although the invention is illustrated and described herein as embodied in a process for the chemical mechanical polishing of wafers, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWINGS

The sole drawing FIGURE diagrammatically depicts a device used to carry out the process according to the invention.

DESCRIPTION OF THE PREFERRED EMBODIMENTS

Referring now to the sole drawing FIGURE in detail, there is diagrammatically shown a device for carrying out the inventive process. First of all, a CMP slurry is provided in a tank 1. The CMP slurry has a specific composition. Furthermore, ranges of values are defined for the substances that are present in the CMP slurry and for impurities, within which ranges, fluctuations can be tolerated without any risk of adverse effect on the quality of the wafers processed. The ranges of values for these components are stored in a process computer 4, by means of which the further operations and parts of the system are also controlled. The CMP slurry can be removed from the tank 1 via line 3 using the pump 2. The quantity removed can be controlled by the process computer 4, which is connected to the pump 2 via a control line 5. The line 3 leads to a sampling point 6, where a sample of the CMP slurry is removed at regular intervals. The quantity of the sample removed and the sampling interval are controlled by the process computer 4, which is connected to the sampling point 6 via control line 7. The CMP slurry sample removed is fed to a sample vessel 9 via sample line 8. The sample vessel 9 consists of an inert material, for example a plastic, in order to prevent the sample from being contaminated. The sample vessel 9 is situated in the turntable 10 of an automatic sampler that is controlled by the control unit 11. The control unit 11 is connected to the process computer 4 via control line 12.

To prepare for the analysis, the turntable 10 is rotated and a certain quantity of a standard is added from the tank 13 for a standard. In general, the procedure is that one sample without a standard and at least two samples with different quantities of standard added are measured. The addition of the standard is controlled by the control unit 11. The sample table is then rotated onward and the sample is homogenized by ultrasound as a result of introducing an ultrasonic generator into the sample. After homogenization, the sample table 10 is rotated onward and a certain quantity of sample, generally a few microliters, is removed from the sample vessel 9 by a sample remover 15. The sample is added to the atomization tube 16 of an electrothermal atomic absorption spectrometer (ETAAS) 17. Then, a temperature program is run, in which first of all the volatile constituents of the sample are evaporated. If necessary, this may be followed by the ashing of low-volatility constituents. This is followed by atomization and spectral analysis of the sample. The measured values can be evaluated in an evaluation unit of the ETAAS 17, or as in the device illustrated, in the process computer 4. For this purpose, the measured values for the components of the CMP slurry that are of interest are transmitted to the process computer 4 via data line 18, where they are compared with the previously defined range of values for the individual components. If the measured value, or in the case of a plurality of components that are of interest, the measured values is/are within the previously defined range of values, the process computer 4 transmits a signal to the valve 20 via control line 19, and the CMP slurry is fed via feed line 21 to a CMP device 22 for the chemical mechanical polishing of wafers.

In this polishing device 22, wafers 23 are ground and polished using the CMP slurry. The polishing operation is likewise controlled using the process computer 4, which is connected to the CMP device 22 via control line 24. If the value determined for the component(s) determined using the ETAAS 17 is outside the defined range of values, the process computer 4 transmits a signal to the valve 20 via control line 19, and the CMP slurry is fed to a temporary storage tank 26 via line 25. There, the CMP slurry can either be topped off by suitable components that are supplied via feed lines 27 and can then fed back to the storage tank 1 via transfer line 28, or if appropriate after suitable treatment, the CMP slurry can be removed from the temporary storage tank 26 via outlet line 29 and discarded. The topping off of the CMP slurry that has been collected in the temporary storage tank 26 can also be controlled by the process computer 4. The process computer 4 may also comprise a memory for data storage, so that the measurement data can be documented and analyzed at a later time, in order, for example, to be able to correlate deviations in the composition of the CMP slurry with fluctuations in quality during the processing of the wafers.

The following text gives an example of a temperature program which is run during the analysis of the sample in the electrothermal atomic absorption spectrometer 17. The quality of sample which is added to the atomization tube 16 is in this case 20 µl.
1.) Drying: 130° C., 2 min;
2.) If appropriate, ashing: 1000° C., 10 s;
3.) Atomization: 2500° C., 5 s including background correction, e.g. Zeeman background correction;
4.) Completion of heating: 2650° C., 3 s; and
5.) Cooling to 20° C.: approx. 2 min.

The temperature program is dependent on the analysis unit used and on the specimen that is to be analyzed and can be modified accordingly.

I claim:

1. A process for chemically mechanically polishing wafers, which comprises:
    providing a CMP slurry having a solvent and at least one component being an interfering ion selected from the group consisting of inorganic salts and ceramic abrasives;
    defining a range of values for a level of the component in the CMP slurry;
    taking a slurry sample from the CMP slurry;
    with an electrothermal absorption spectrometer, performing electrothermal slurry atomic absorption spectrometry to obtain a determined level of the component in the slurry sample;
    comparing the determined level of the component with the range of values for the level of the component;
    if the determined level of the component is within the range of values for the level of the component, feeding the CMP slurry to a CMP device and polishing a wafer using the CMP slurry in the CMP device; and
    if the determined level of the component is outside the range of values for the level of the component, triggering a signal and feeding the CMP slurry to a temporary storage device.

2. The process according to claim 1, which comprises homogenizing the slurry sample using ultrasound before carrying out the step of performing the electrothermal slurry atomic absorption spectrometry to obtain the determined level of the component in the slurry sample.

3. The process according to claim 2, which comprises performing the step of homogenizing the slurry sample at a frequency of between 40 and 50 kHz, at a power of 2 to 10 watts, and for a period of 10 to 60 seconds.

4. The process according to claim 1, which comprises:
    performing the step of defining the range of values such that the range of values is less than 10 ppm.

5. The process according to claim 4, which comprises performing the step of defining the range of values such that the range of values is less than 100 ppb.

6. The process according to claim 4, which comprises performing the step of defining the range of values such that the range of values is less than 1 ppb.

7. The process according to claim 4, which comprises providing the interfering ion as an ion of at least one element selected from a group consisting of Al, Ca, Cr, Cu, Fe, K, Mg, Na, Ni, and Zn.

8. The process according to claim 1, which comprises using an automatic sampler to feed the slurry sample to the electrothermal absorption spectrometer.

9. The process according to claim 1 which comprises:
    defining a maximum deviation for the component;
    for the CMP slurry that has been fed to the temporary storage device, determining a difference between the determined level and the range of values for the level;
    if the difference is less than the maximum deviation, adding more of the component until the level of the component lies within the range of values; and
    if the difference is greater than the maximum deviation, discarding the CMP slurry.

10. The process according to claim 1, which comprises carrying out the step of performing the electrothermal slurry atomic absorption spectrometry on line so that the CMP slurry can be fed to the CMP device.

11. The process according to claim 1, which comprises using a process computer to control the steps of:
    performing the electrothermal slurry atomic absorption spectrometry to obtain the determined level of the component in the slurry sample; and
    feeding of the CMP slurry to the CMP device.

* * * * *